(12) United States Patent
Beaupre

(10) Patent No.: US 11,420,358 B2
(45) Date of Patent: Aug. 23, 2022

(54) METHODS AND SYSTEM FOR HANDLING FRESH CONCRETE

(71) Applicant: COMMAND ALKON INCORPORATED, Birmingham, AL (US)

(72) Inventor: Denis Beaupre, Saint-Catherine-de-la-Jacques (CA)

(73) Assignee: Command Alkon Incorporated, Birmingham, AL (US)

( * ) Notice: Subject to any disclaimer, the term of this patent is extended or adjusted under 35 U.S.C. 154(b) by 690 days.

(21) Appl. No.: 16/468,473

(22) PCT Filed: Dec. 20, 2017

(86) PCT No.: PCT/EP2017/083937
§ 371 (c)(1),
(2) Date: Jun. 11, 2019

(87) PCT Pub. No.: WO2018/115192
PCT Pub. Date: Jun. 28, 2018

(65) Prior Publication Data
US 2020/0078987 A1 Mar. 12, 2020

Related U.S. Application Data

(60) Provisional application No. 62/437,754, filed on Dec. 22, 2016.

(51) Int. Cl.
*B28C 7/02* (2006.01)
*G01N 11/14* (2006.01)
*G01N 33/38* (2006.01)

(52) U.S. Cl.
CPC .............. *B28C 7/024* (2013.01); *G01N 11/14* (2013.01); *G01N 33/383* (2013.01)

(58) Field of Classification Search
CPC ... B01F 15/00246; B60P 3/16; G01N 33/383; G01N 2011/0046; G01N 11/00; G01N 11/10
See application file for complete search history.

(56) References Cited

U.S. PATENT DOCUMENTS 2,643,542 A * 6/1953 Cronk .................... G01N 11/00
73/54.03
3,147,612 A * 9/1964 Evans .................... G01N 11/10
73/54.23

(Continued)

FOREIGN PATENT DOCUMENTS

JP S5916531 A 1/1984
JP S6150601 A 3/1986

(Continued)

OTHER PUBLICATIONS

Beaupre, Denis. "Mixer-Mounted Probe Measures Concrete Workability." Concrete International, Sep. 2012, 4 pages.

(Continued)

*Primary Examiner* — David A. Rogers
(74) *Attorney, Agent, or Firm* — Norton Rose Fulbright US LLP

(57) ABSTRACT

The method of handling fresh concrete generally includes the steps of receiving a viscosity value of the fresh concrete and a pressure value of a pressure exerted on a Theological probe moving in the fresh concrete; using a processor, accessing at least two calibration data sets, the at least two calibration data sets including combinations of different reference pressure values and associated reference workability values for a corresponding one of at least two reference viscosity values; determining a viscosity difference value by comparing the received viscosity value to the at least two reference viscosity values; and determining a workability value of the workability of the fresh concrete (Continued)

based on the reference workability values associated with reference pressure values corresponding to the received pressure value in the at least two calibration data sets and on the viscosity difference value; and handling the fresh concrete based on the determined workability value.

14 Claims, 11 Drawing Sheets

(56) References Cited

U.S. PATENT DOCUMENTS

| | | | |
|---|---|---|---|
| 3,237,437 A * | 3/1966 | Hilkemeier | G01N 33/26 73/54.03 |
| 3,403,546 A * | 10/1968 | Stratton | G01N 11/10 73/862.194 |
| 3,640,121 A * | 2/1972 | Mercier | G01N 33/26 73/54.03 |
| 4,193,291 A * | 3/1980 | Lynnworth | G01N 9/00 376/245 |
| 4,356,723 A * | 11/1982 | Fay | G01N 11/00 73/54.03 |
| 4,578,989 A * | 4/1986 | Scott | G01N 33/383 33/379 |
| 4,900,154 A * | 2/1990 | Waitzinger | G01N 33/383 366/40 |
| 5,086,646 A * | 2/1992 | Jamison | G01N 9/00 73/61.63 |
| 5,541,855 A * | 7/1996 | Enzler | G01N 11/14 73/803 |
| 6,918,292 B2 * | 7/2005 | Go Boncan | G01N 33/383 73/866 |
| 6,957,586 B2 * | 10/2005 | Sprague | G01F 1/3259 73/32 R |
| D638,729 S * | 5/2011 | Beaupre | D10/78 |
| 8,764,272 B2 * | 7/2014 | Hazrati | G01N 33/383 700/265 |
| 9,199,391 B2 * | 12/2015 | Beaupre | B28C 7/024 |
| 9,429,559 B2 * | 8/2016 | Radjy | G01N 33/383 |
| 9,518,870 B2 * | 12/2016 | Verdino | G01K 1/024 |
| 9,702,863 B2 * | 7/2017 | Beaupré | G01N 33/383 |
| 9,789,629 B2 * | 10/2017 | Koehler | G05D 21/02 |
| 9,833,928 B2 * | 12/2017 | Bonilla Benegas | B60P 3/16 |
| 10,041,928 B2 * | 8/2018 | Berman | B28C 7/024 |
| 10,052,794 B2 * | 8/2018 | Beaupré | B28C 7/12 |
| 10,126,288 B2 * | 11/2018 | Radjy | G01N 33/383 |
| 10,156,547 B2 * | 12/2018 | Biesak | G01N 29/045 |
| 10,429,285 B2 * | 10/2019 | Uusivirta | G01N 11/00 |
| 10,520,410 B2 * | 12/2019 | Beaupre | G01N 11/14 |
| 10,527,534 B2 * | 1/2020 | McAnally | G01N 29/348 |
| 10,739,328 B2 * | 8/2020 | Baird | G01N 33/18 |
| 10,877,017 B2 * | 12/2020 | Radjy | G01N 33/383 |
| 10,989,643 B2 * | 4/2021 | Beaupre | G01N 29/024 |
| 11,041,794 B2 * | 6/2021 | Beaupre | G01N 11/00 |
| 11,123,896 B2 * | 9/2021 | Beaupre | C04B 40/0028 |
| 11,230,217 B2 * | 1/2022 | Beaupre | B28C 5/422 |
| 11,275,009 B2 * | 3/2022 | Biesak | G01N 33/383 |
| 2005/0087002 A1 * | 4/2005 | Kanzaki | B01F 33/453 73/54.28 |
| 2009/0171595 A1 * | 7/2009 | Bonilla Benegas | B28C 5/422 702/41 |
| 2012/0016523 A1 * | 1/2012 | Koehler | G01N 11/00 700/265 |
| 2014/0297204 A1 * | 10/2014 | Biesak | G01N 29/4436 702/56 |
| 2015/0212061 A1 * | 7/2015 | Radjy | G01N 33/383 73/53.01 |
| 2015/0355160 A1 | 12/2015 | Berman | |
| 2016/0018383 A1 * | 1/2016 | Radjy | G01N 33/383 73/53.01 |
| 2016/0025700 A1 * | 1/2016 | Beaupré | B28C 5/422 73/32 R |
| 2016/0223512 A1 * | 8/2016 | Radjy | G01N 25/20 |
| 2016/0250775 A1 * | 9/2016 | Chun | C04B 28/02 524/5 |
| 2017/0108421 A1 * | 4/2017 | Beaupre | G01N 11/10 |
| 2017/0212094 A1 * | 7/2017 | Radjy | G01N 33/383 |
| 2017/0219553 A1 * | 8/2017 | Radjy | G01N 33/383 |
| 2018/0100791 A9 * | 4/2018 | Beaupre | G01N 11/14 |
| 2020/0217833 A1 * | 7/2020 | Davis | G01N 29/245 |
| 2020/0232966 A1 * | 7/2020 | Beaupre | G01N 33/383 |
| 2021/0031407 A1 * | 2/2021 | Roberts | G01N 11/14 |
| 2021/0055195 A1 * | 2/2021 | Beaupre | B28C 7/024 |

FOREIGN PATENT DOCUMENTS

| | | | | |
|---|---|---|---|---|
| JP | H02208564 A | 8/1990 | | |
| JP | H0426537 A | 1/1992 | | |
| JP | 2008049499 A | 3/2008 | | |
| JP | 2012091729 A | 5/2012 | | |
| JP | 2016539022 A | 12/2016 | | |
| WO | WO-2005029045 A1 * | 3/2005 | | G01N 11/14 |
| WO | WO-2007060272 A3 * | 7/2007 | | B01F 15/00207 |
| WO | WO 2010/110814 A1 | 9/2010 | | |
| WO | WO 2015/057380 A1 | 4/2015 | | |
| WO | WO 2017/099711 A1 | 6/2017 | | |

OTHER PUBLICATIONS

Japanese Patent Office, Office Action issued for Japanese Patent Application No. 2019-534687, dated Mar. 30, 2021, 6 pages.

* cited by examiner

| Vr1 ||
| --- | --- |
| REFERENCE PRESSURE VALUE Pr1 (kPa) | REFERENCE WORKABILITY VALUE Wr1 (cm) |
| 0.01 | 47 |
| 1 | 39 |
| 2.4 | 31 |
| 4.6 | 22 |
| 7 | 18 |
| 11 | 13 |
| 15 | 9 |
| 40 | 1 |

FIG-2

| Vr2 ||
| --- | --- |
| REFERENCE PRESSURE VALUE Pr2 (kPa) | REFERENCE WORKABILITY VALUE Wr2 (cm) |
| 0.01 | 27 |
| 1 | 24 |
| 2.4 | 21 |
| 4.6 | 18 |
| 7 | 15 |
| 11 | 11 |
| 15 | 8 |
| 40 | 0 |

FIG-4

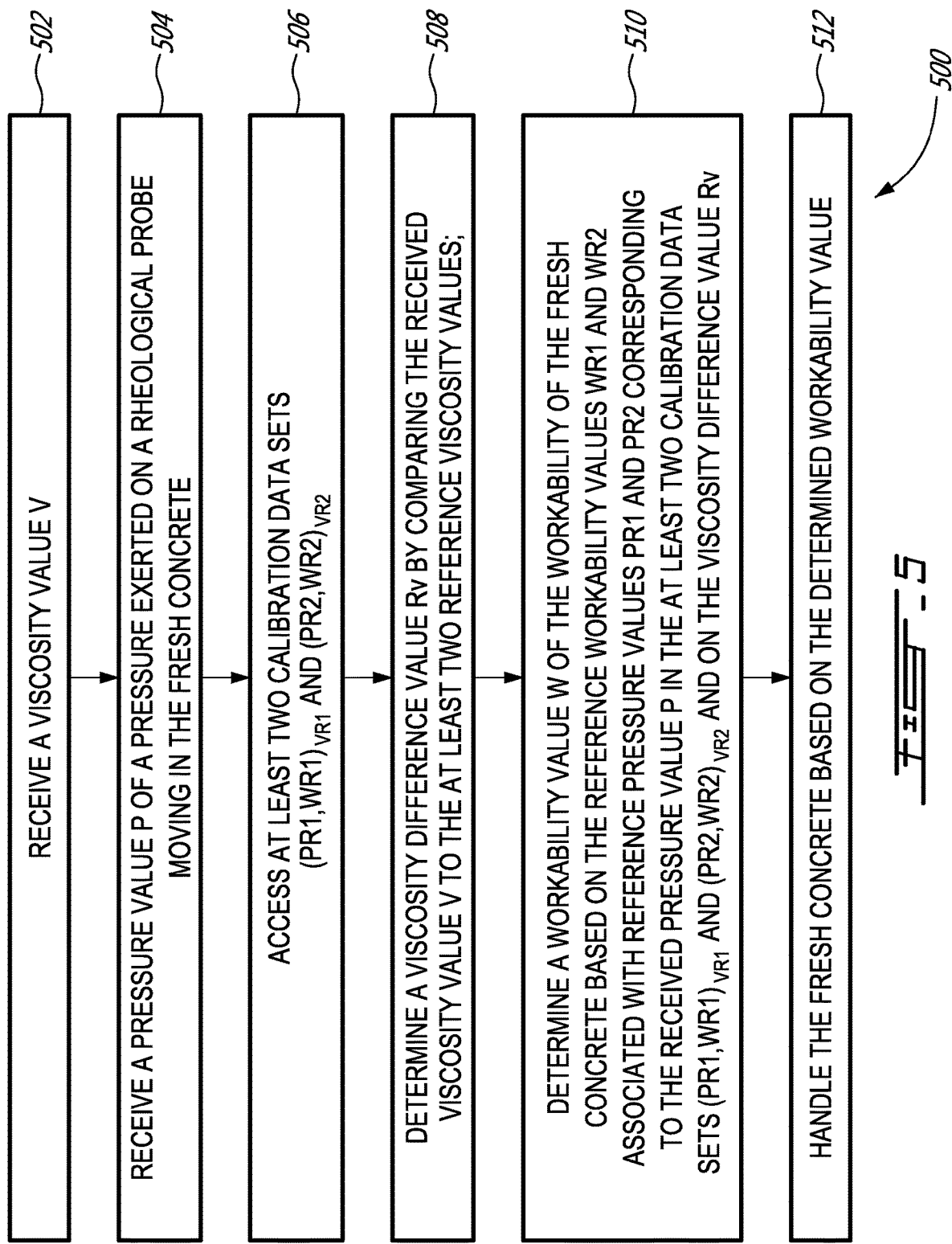

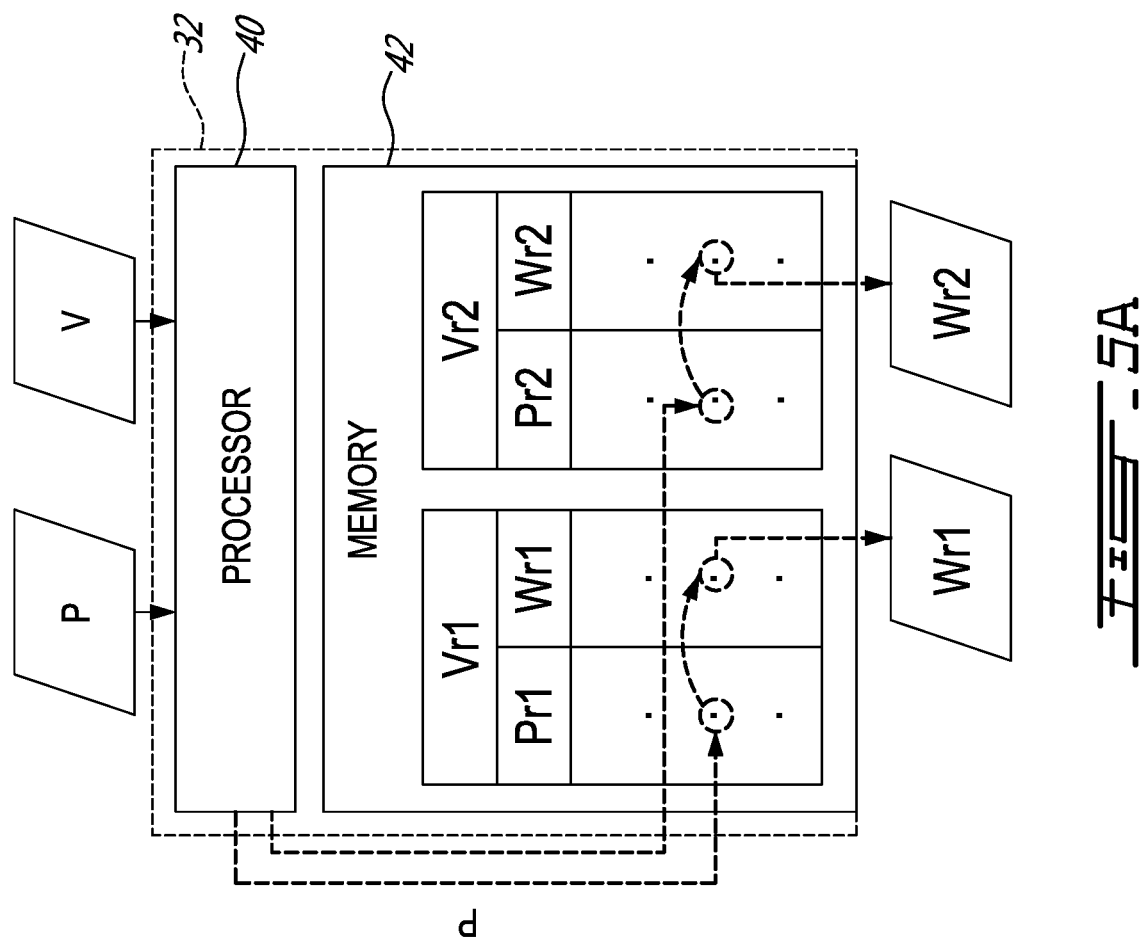

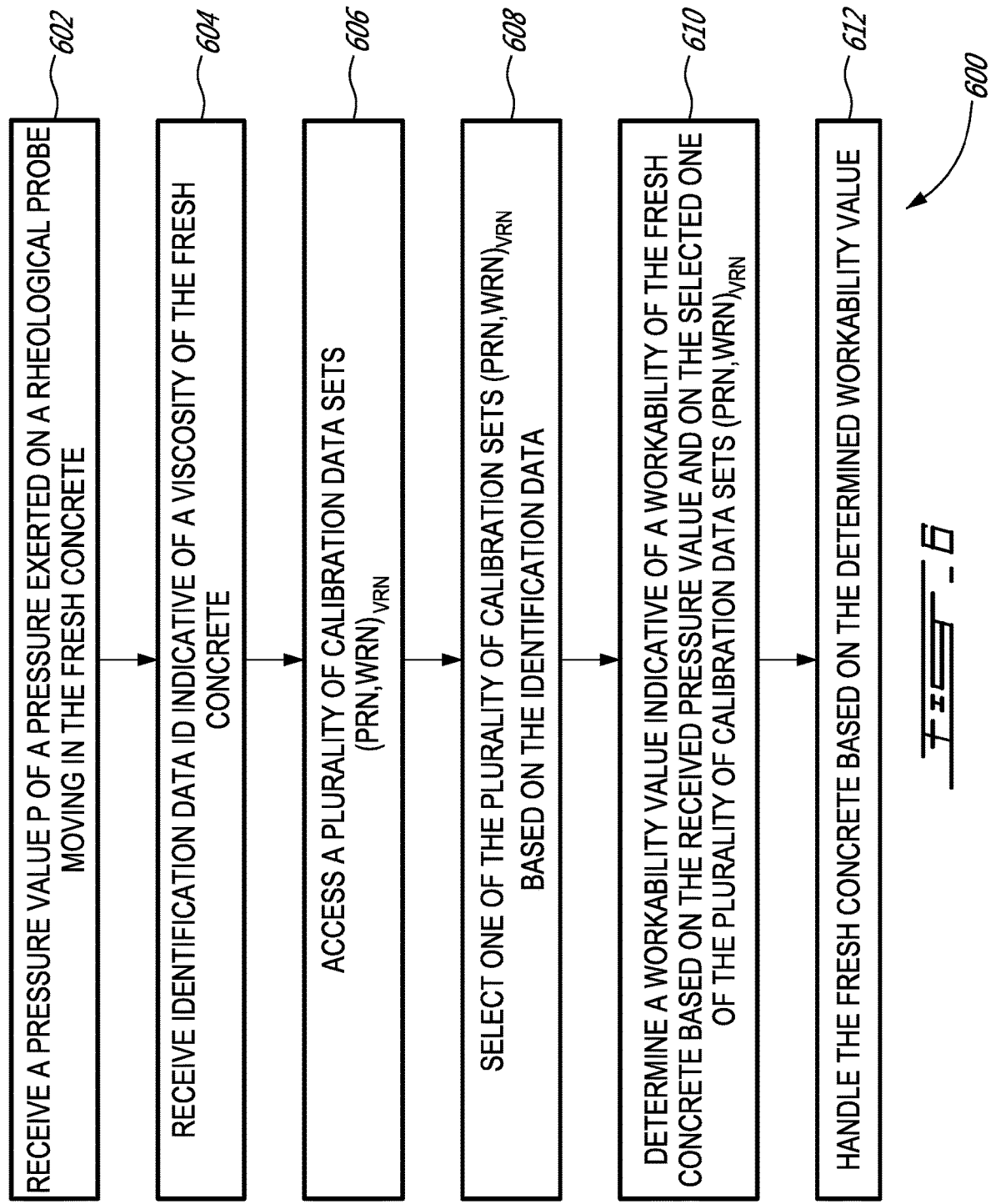

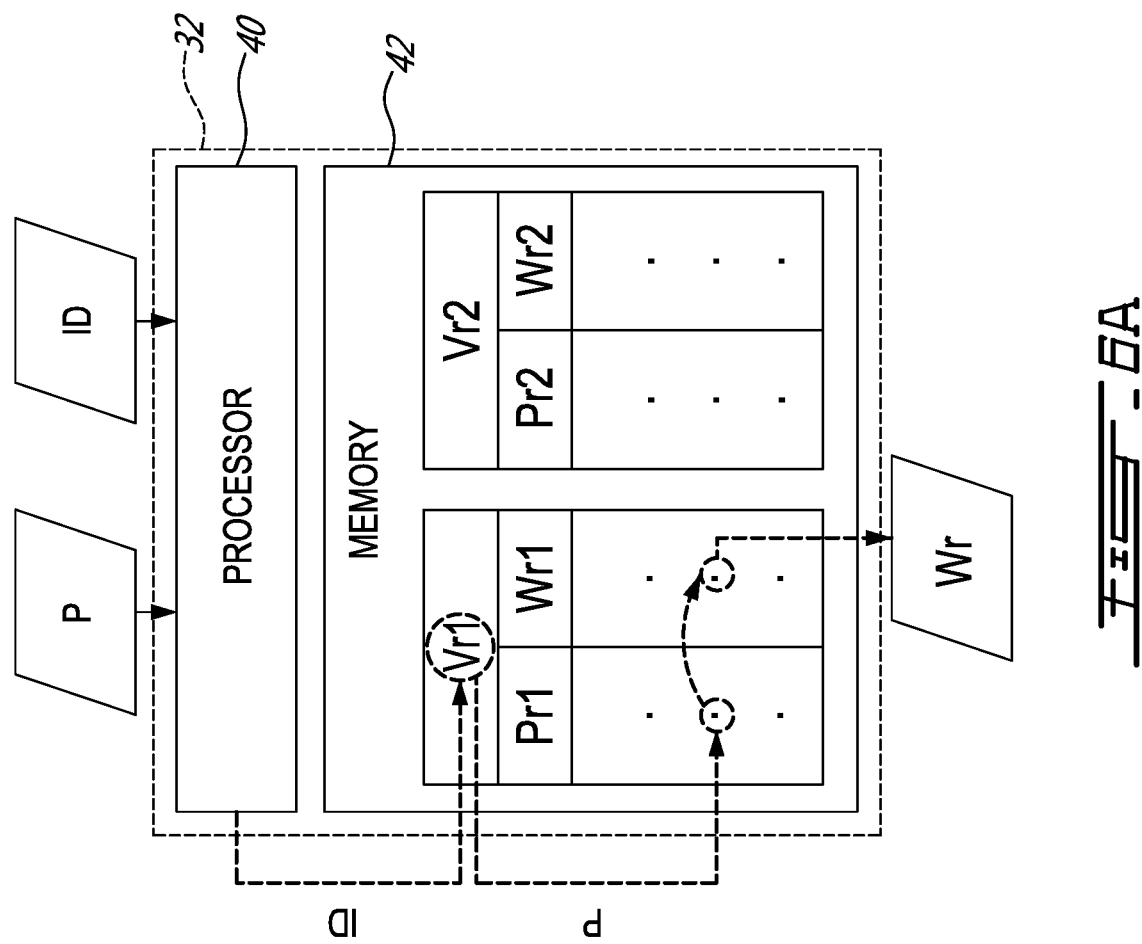

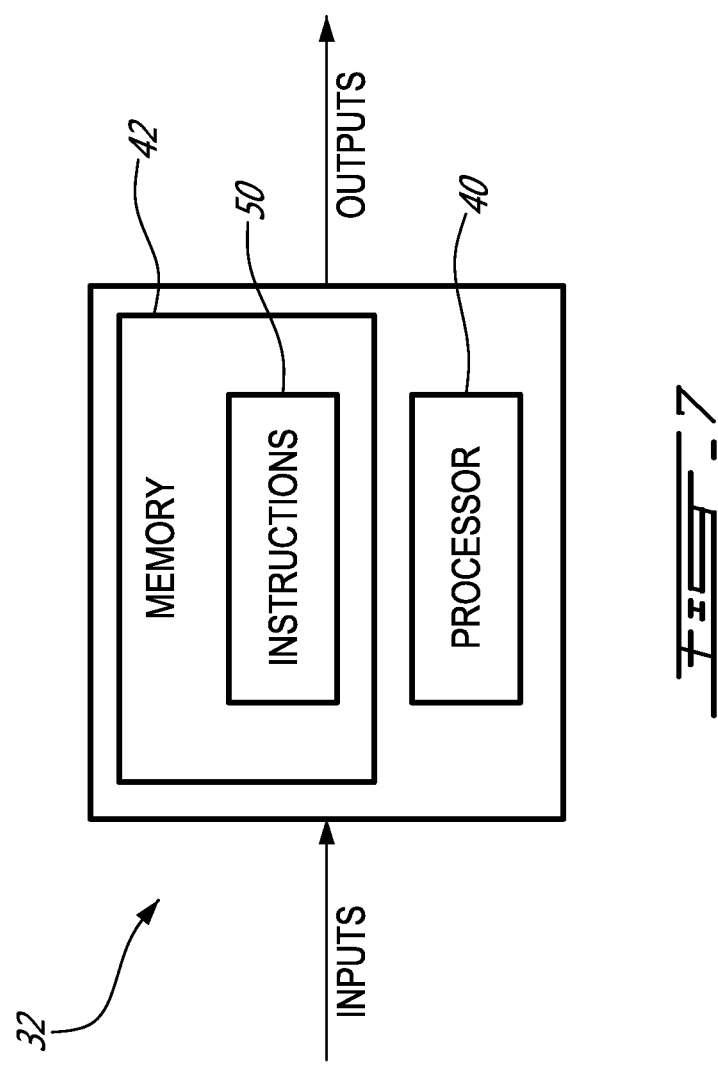

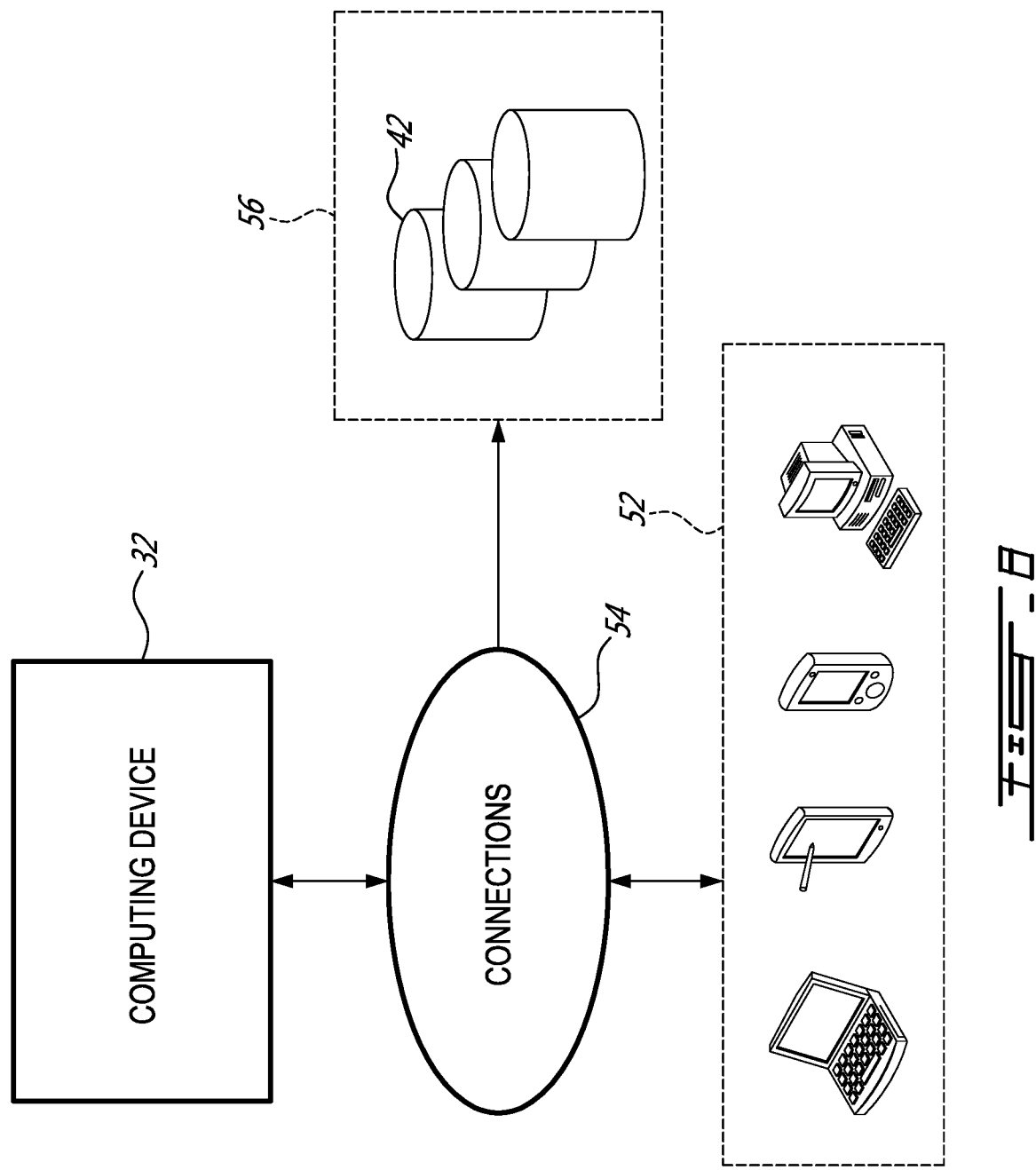

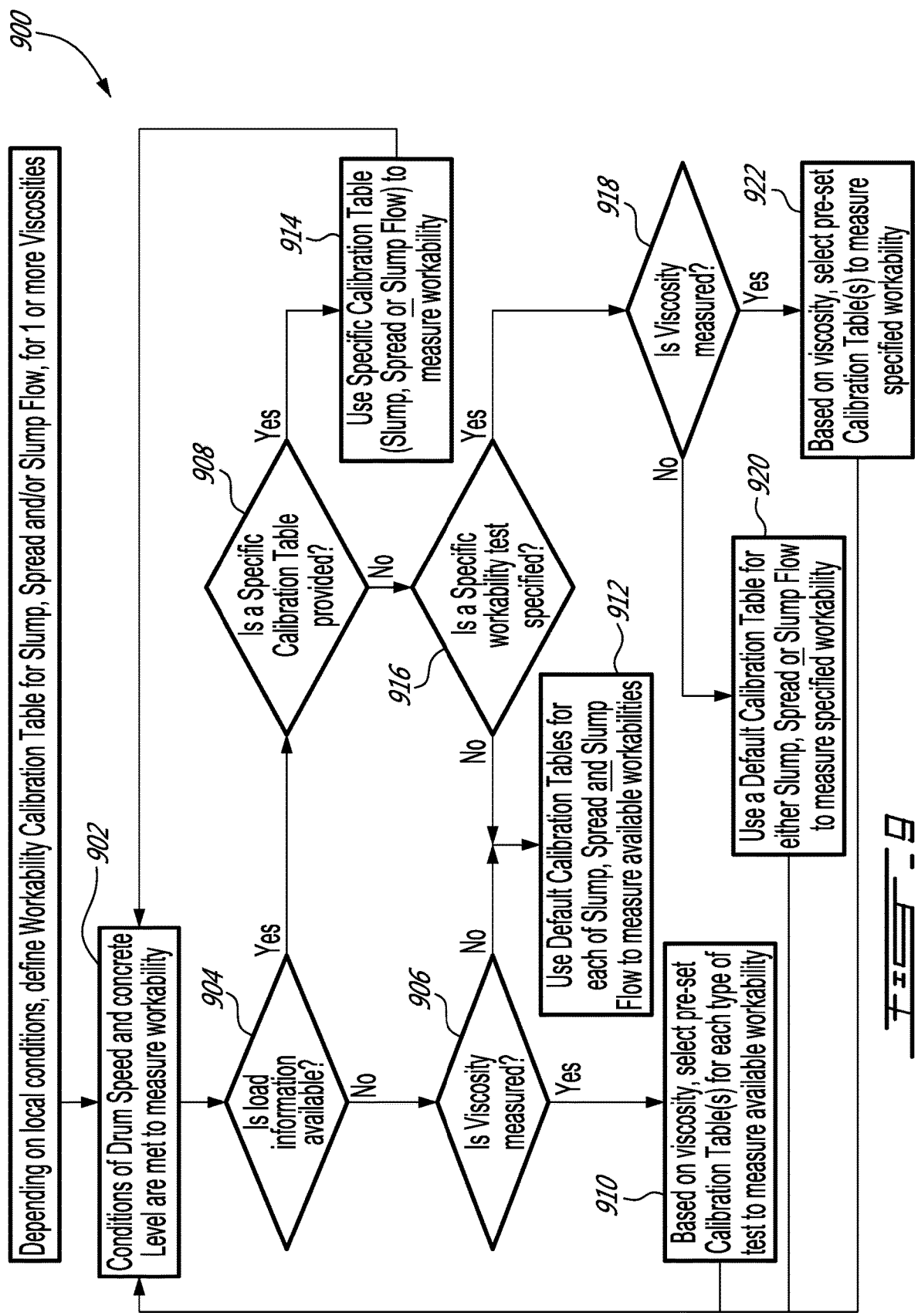

METHODS AND SYSTEM FOR HANDLING FRESH CONCRETE

This application is a national phase application under 35 U.S.C. § 371 of International Application No. PCT/EP2017/083937 filed Dec. 20, 2017, which claims priority to United States Provisional Patent Application No. 62/437,754 filed Dec. 22, 2016. The entire contents of each of the above-referenced disclosures is specifically incorporated by reference herein without disclaimer.

FIELD

The improvements generally relate to the handling of fresh concrete and more particularly to methods of determining the workability of the fresh concrete.

BACKGROUND

With reference to FIG. 1, fresh concrete 10 is formed of a mixture of ingredients including at least cement-based material and water in given proportions. The ingredients are typically transported inside a drum 12 of a mixer truck 14 where the fresh concrete 10 can be mixed prior to pouring thereof.

During handling of the fresh concrete, achieving and/or maintaining a satisfactory workability is a concern. It is commonplace in the field to obtain an indication of workability by performing a workability test. The workability can then be adjusted by adding water, aggregates and/or admixtures to the fresh concrete.

Some of these workability tests have been standardized such as the slump test JIS1100, the spread test DIN EN 12350, the slump flow tests ASTMC143 and BS EN12350. Generally, in these standard workability tests, a person is required to draw a sample of fresh concrete, manipulate it in a given way and deduce a workability value based on how the fresh concrete reacts to the manipulations.

In recent years, rheological probes were developed to circumvent some drawbacks associated with the standard workability tests. For instance, these tests were found to be time- and resource-consuming in addition to the fact that manipulation errors could account for a substantial bias in the measured workability. For instance, international publication WO 2011/042880 discloses an example of a rheological probe for use in determining the workability of fresh concrete in a drum of a concrete mixer. Although existing rheological probes are satisfactory to a certain extent, there remains room for improvement.

SUMMARY

As shown in FIG. 1, a rheological probe 18 is mounted inside the drum 12 of the mixer truck 14 to measure rheological properties such as workability, viscosity and the like as the drum 12 rotates, as described in international publication WO 2011/042880. More specifically, in the case of workability, the workability of the fresh concrete 10 can be determined by measuring a pressure value indicative of a pressure exerted on the rheological probe 18 by the fresh concrete 10 and then by comparing the measured pressure value to a predetermined calibration table including combinations of different reference pressure values Pr1 and associated reference workability values Wr1.

The calibration table 20 can be predetermined through a calibration process. An example of a calibration process is described for ease of understanding. In this example, a standard mixture of fresh concrete is first prepared so as to be relatively stiff. For instance, at the beginning of the calibration process, the fresh concrete has a slump of 30 to 50 mm (1.25 to 2 in) or a spread of 300 mm (11.75 in). The calibration mixture is incrementally modified by adding water, and data points are collected by intermediate measurements at each increment, until the calibration mixture reaches a point of complete collapse. For instance, the water can be added in increments of 10 L/m$^3$ (2 gal/yd$^3$). After each incremental addition of water, the drum is rotated at a mixing speed for at least 3 minutes. When mixing is completed, reference pressure values Pr1 are measured by the rheological probe while the drum is turned at a calibration speed such as two revolutions per minute for at least three turns in order to obtain a reference pressure value. At the same time, two independent standard workability tests are conducted to obtain a reference workability value Wr1. The calibration table 20 is built incrementally by associating each reference workability value Wr1 with its corresponding reference pressure value Pr1. Generally, the calibration speed is chosen to be a low speed, such as a speed at which the effects of yield stress on pressure are predominant over the effects of viscosity.

Once the calibration table 20 has been prepared, it can then be used by a system to determine workability of ready-mix concrete. More specifically, the pressure is measured by the probe at a given 'test speed', and the pressure measurement can be used as a key to find the corresponding workability value in the calibration table 20. The test speed can affect the precision of the workability value so obtained. For instance, if the probe is moved at a high test speed (e.g., between 1.5 and 2 m/s), in a context where the calibration speed was a low speed (e.g., between 0.25 and 0.75 m/s), the effects of viscosity on pressure, which typically increase linearly with speed, may significantly bias the pressure reading resulting from the high test speed, and lead to an inadequate match in the calibration table. When the test speed is low, the effects of viscosity on pressure are low, and the effect of yield stress on pressure can be predominant. In such cases, even if the test speed is not perfectly equal to the calibration speed, the effect of the difference between the test speed and the calibration speed on the pressure can be negligible. Accordingly, it can be practical to choose a low speed both for the calibration speed and the test speed. Alternatively, a higher calibration speed can also lead to satisfactory results. For instance, if a higher calibration speed is used, and the test speed is monitored to ensure that it is equal to the calibration speed, the pressure reading obtained at the test speed can lead to a satisfactory match in the calibration table.

The tangential speed of the probe 18 in the concrete 10 can be can be calculated based on a dimension (e.g., a circumference) of the drum 12 and a number of RPM of the drum 12.

FIG. 2 shows an example of the calibration table 20 whereas FIG. 3 shows a calibration curve 22 based on the reference pressure values Pr1 and on the reference workability values Wr1 of the calibration table 20.

It was found that using a unique calibration table for different mixtures of fresh concrete can introduce biases in the resulting workability measurements, especially when the mixtures are for high strength concrete or when the mixtures include cement replacement such as slap. The biases can be particularly significant especially when the mixture under test has a viscosity which differs significantly from the reference viscosity value Vr1 of the mixture with which the calibration table 20 was originally determined. It was found that this problem can be alleviated by using two or more calibration tables, where each calibration table is associated with a respective reference viscosity value Vr.

For instance, FIG. 4 shows a second calibration table 26 including combinations of reference pressure values Pr2 and associated reference workability values Wr2 for a fresh concrete having a reference viscosity value V2 different than that of the standard mixture associated with the first calibration table 20 of FIG. 2, i.e. the reference viscosity value Vr1. As can be seen in FIG. 3, a second calibration curve 28 based on the second calibration table 26 is shown next to the first calibration curve 22 based on the first calibration table 26. It can be understood that for a given reference pressure value, e.g., Pr1, the reference workability values Wr1 and Wr2 associated with the given reference pressure value Pr1 differ from one another depending on which one of the calibration curves 22 and 28 is used. Therefore, selecting the right calibration curve or table can reduce the error in the workability measurement, especially when the measured pressure value of the fresh concrete decreases.

In accordance with one aspect, there is provided a method of handling fresh concrete comprising: receiving a viscosity value of the fresh concrete and a pressure value of a pressure exerted on a rheological probe moving in the fresh concrete; using a processor, accessing at least two calibration data sets, the at least two calibration data sets including combinations of different reference pressure values and associated reference workability values for a corresponding one of at least two reference viscosity values; determining a viscosity difference value by comparing the received viscosity value to the at least two reference viscosity values; and determining a workability value of the workability of the fresh concrete based on the reference workability values associated with reference pressure values corresponding to the received pressure value in the at least two calibration data sets and on the viscosity difference value; and handling the fresh concrete based on the determined workability value.

As described below, the handling of the fresh concrete can include adding ingredients to the fresh concrete, further mixing the fresh concrete and/or pouring the fresh concrete, depending on the embodiment.

In accordance with another aspect, there is provided a system comprising: at least one rheological probe mounted to a concrete mixer, the rheological probe being configured to measure a pressure value of a pressure exerted on the at least one rheological probe moving in fresh concrete inside the concrete mixer; a computing device communicatively coupled with the rheological probe, the computing device being configured for performing the steps of receiving a viscosity value of the fresh concrete; accessing at least two calibration data sets stored on a memory accessible by the computing device, the at least two calibration data sets including combinations of different reference pressure values and associated reference workability values for a corresponding one of at least two reference viscosity values; determining a viscosity difference value by comparing the received viscosity value to the at least two reference viscosity values; and determining a workability value of the workability of the fresh concrete based on the reference workability values associated with reference pressure values corresponding to the measured pressure value in the at least two calibration data sets and on the viscosity difference value; and a user interface communicatively coupled with the computing device, the user interface being configured to output a signal indicative of the workability value of the fresh concrete.

In accordance with another aspect, there is provided a method of handling fresh concrete comprising: receiving a pressure value of a pressure exerted on a rheological probe moving in the fresh concrete; receiving identification data indicative of a viscosity of the fresh concrete; using a processor, accessing a plurality of calibration data sets, the calibration data sets including combinations of different reference pressure values and associated reference workability values for fresh concrete having a respective one of a plurality of different reference viscosities; selecting one of the plurality of calibration data sets based on the identification data; and determining a workability value indicative of a workability of the fresh concrete based on the received pressure value and on the selected one of the plurality of calibration data sets; and handling the fresh concrete based on the determined workability value.

In accordance with another aspect, there is provided a system comprising at least one rheological probe mounted to a concrete mixer, the rheological probe being configured to measure a pressure value of a pressure exerted on the at least one rheological probe moving in fresh concrete inside the concrete mixer; computing device communicatively coupled with the rheological probe, the computing device being configured for performing the steps of receiving identification data indicative of a viscosity of the fresh concrete; accessing a plurality of calibration data sets, the calibration data sets including combinations of different reference pressure values and associated reference workability values for fresh concrete having a respective one of a plurality of different reference viscosities; selecting one of the at least two calibration data sets based on the identification data; and determining a workability value indicative of a workability of the fresh concrete based on the measured pressure value and on the selected one of the plurality of calibration data sets; and a user interface communicatively coupled with the computing device, the user interface being configured to output a signal indicative of the workability value of the fresh concrete.

It will be noted that in a computerized system, a calibration table can be used, or a calibration curve can be provided in the form of an equation interpolated from experimental points of a calibration table, and used instead of a calibration table, for instance. However, it was found that using calibration data sets (e.g., calibration data sets) can be easily stored on the memory and can simplify the program instructions to be performed by the processor.

Many further features and combinations thereof concerning the present improvements will appear to those skilled in the art following a reading of the instant disclosure.

DESCRIPTION OF THE FIGURES

In the figures,

FIG. 2 is a table showing a standard calibration data set for a standard mixture of fresh concrete, in accordance with an embodiment;

FIG. 4 is a graph showing a second calibration data set for a mixture of fresh concrete different from the standard mixture of fresh concrete associated with the standard calibration data set of FIG. 2, in accordance with an embodiment;

FIG. 5 is a flowchart of a first method of handling fresh concrete, in accordance with an embodiment;

FIG. 5A is a block diagram of an example of a computing device performing the first method of FIG. 5, in accordance with an embodiment;

FIG. 6 is a flowchart of a second method of handling fresh concrete, in accordance with an embodiment;

FIG. 6A is a block diagram of an example of a computing device performing the second method of FIG. 6, in accordance with an embodiment;

FIG. 7 is a block diagram of an example of a computing device;

FIG. 8 is a diagram illustrating an example system for determining a workability value of fresh concrete, in accordance with an embodiment; and FIG. 9 is a flowchart of an example method of determining a workability value of fresh concrete, in accordance with an embodiment.

DETAILED DESCRIPTION

Figure 1:
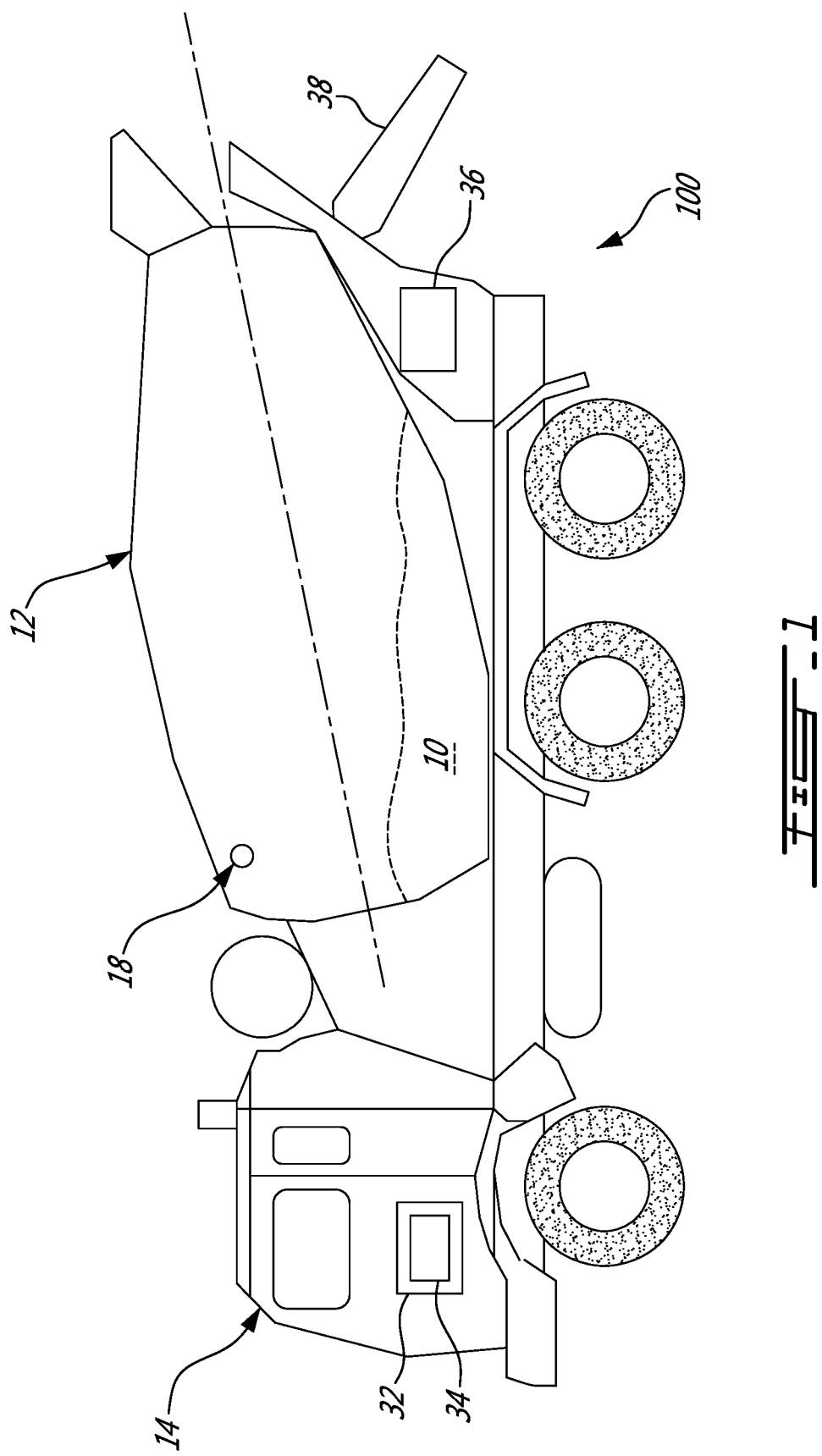
FIG. 1 is a schematic view of an example of a system for determining a workability value of fresh concrete inside a drum of a mixer truck, in accordance with an embodiment.

FIG. 1 shows an example of a concrete mixer used for handling of fresh concrete. As depicted, the concrete mixer is embodied as a mixer truck 14 having a rotatable drum 12 configured for containing, mixing and pouring fresh concrete 10 via a discharge chute 38. During use, it is generally desirable to obtain an indication of the workability of the fresh concrete 10 before pouring. Accordingly, ingredients can be added to the fresh concrete 10 to modify its workability towards a target workability value. When it is determined that the workability of the fresh concrete 10 corresponds to the target workability value, the fresh concrete 10 can be poured at a desired location for it to harden into a desired structure.

A system 100 is provided for determining a workability value of the fresh concrete 10 while it is being handled (e.g., mixed or poured), by the mixer truck 14. In the illustrated example, the system 100 includes the rheological probe 18 mounted inside the drum 12. The rheological probe 18 is configured to measure a pressure value of a pressure exerted on a body of the rheological probe 18 moving in the fresh concrete 10 when the drum 12 turns at a rotational speed corresponding to the calibration speed used in the calibration process. Since the calibration speed of the drum in the calibration processes is chosen to be a low speed, the rotational speed of the drum 12 during the pressure value measurement is set at a low speed accordingly. In some embodiments, the pressure value is measured when the drum 12 turns at a rotational speed which makes the rheological probe 18 move at a speed in a low speed range (e.g., between 0.25 and 0.75 m/s). An example of such rheological probe is described in international publication WO 2011/042880. In this example, the rheological probe 18 can also measure a viscosity value of the fresh concrete 10.

In this embodiment, the system 100 includes a computing device 32 communicatively coupled with the rheological probe 18, i.e. the computing device 32 can receive the measured pressure and viscosity values from the rheological probe 18. Accordingly, the rheological probe 18 includes a transmitter for transmitting the measured pressure and/or viscosity values to the computing device 32.

The system 100 includes a user interface 34 typically mounted to the mixer truck 14 and communicatively coupled with the computing device 32. The connection between the computing device 32 and the user interface 34 can be wired or wireless. In some embodiments, this connection is direct but it can also include a transmission across a network such as the Internet, for instance.

In the illustrated embodiment, the computing device 32 is provided in the form of an on-board computer mounted to the mixer truck 14, and the user interface 34 is made integral thereto. In this example, the rheological probe 18 communicates with the computing device 32 via a transceiver 36. The transceiver 36 is mounted to the mixer truck 14 and can act as a receiver for receiving measured pressure and/or viscosity values from the rheological probe 18 and as a transmitter for transmitting the measured pressure and/or viscosity values to the computing device 32. The user interface 34 can include a display, a keyboard, a touch-sensitive display, LED lights, and/or any combination thereof. Any other suitable type of user interface can also be used.

FIG. 2 shows an example of a first calibration data set, illustrated in the form of the first calibration table 20. As depicted, the first calibration table 20 can be inherently referred to as the standard calibration table 20 as it can be obtained through a calibration process using a standard mixture of fresh concrete. Because the standard mixture of fresh concrete is generally characterized by a standard, reference viscosity value Vr1, the standard calibration table 20 can be associated with the reference viscosity value Vr1. In this example, the reference viscosity value Vr1 can be set as a relative viscosity value of 2. In this example, the standard calibration table 20 includes a column with a series of reference pressure values Pr1 and another column with a series of reference workability values Wr1 associated with corresponding ones of the reference pressure values Pr1. For ease of reference, the first calibration data set can thus be identified as $(Pr1,Wr1)_{Vr1}$.

FIG. 4 shows an example of a second calibration data set, illustrated in the form of the second calibration table 26. In this example, the second calibration table 26 has been obtained through a calibration process on a second mixture of fresh concrete different than the standard mixture of fresh concrete. Accordingly, the second mixture of fresh concrete is characterized by a reference viscosity value Vr2 different than the reference viscosity value Vr1. In this example, the reference viscosity value Vr2 can be set as a relative viscosity value of 4, i.e., more viscous than the standard mixture of fresh concrete. In this example, the second calibration table 26 includes a column with a series of reference pressure values Pr2 and another column with a series of reference workability values Wr2 associated with corresponding ones of the reference pressure values Pr2. For ease of reference, the first calibration data set can thus be identified as $(Pr2,Wr2)_{Vr2}$.

Figure 3:
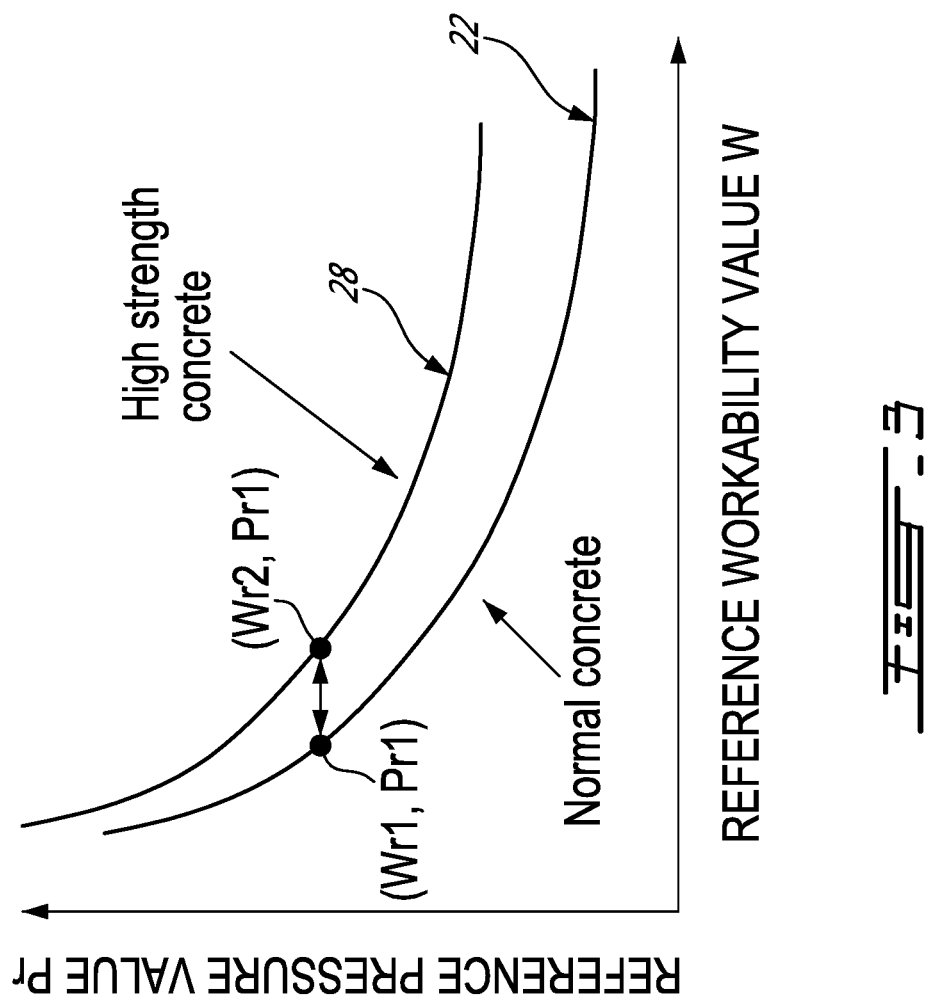
FIG. 3 is a graph showing first and second calibration curves associated with fresh concrete having a respective one of two reference viscosity values, in accordance with an embodiment.

Arbitrarily, in this example, the reference pressure values Pr1 and Pr2 are expressed in units of kilopascals whereas the reference workability values Wr1 and Wr2 are expressed in units of centimeters. However, it is noted that these values can be expressed in any equivalent units. For instance, the reference workability values Wr1 and Wr2 can be expressed in terms of slump values, spread values and/or slump flow values depending on the embodiment. The values of the standard and second calibration tables 20 and 26 are plotted in the graph of FIG. 3 as first and second calibration curves 22 and 28, respectively.

FIG. 5 shows a flowchart of an example of a method 500 of handling fresh concrete. Description of the method 500 will be made with reference to the embodiment shown in FIG. 1, for ease of reading. For instance, the method 500 can be performed by the system 100 in order to determine a workability value W of the fresh concrete and to handle the fresh concrete based on the determined workability value W.

At step 502, the computing device 32 receives a viscosity value V of a viscosity of the fresh concrete. In some embodiments, the viscosity value V is measured by the rheological probe 18 so that the computing device 32 receives the viscosity value V from the rheological probe 18. In some other embodiments, the viscosity value V is inputted into the user interface 34 so that the computing device 32 receives the viscosity value from the user interface 34. For instance, in this example, the viscosity value V can be inputted as being a relative viscosity value of 4.

At step 504, the computing device 32 receives a pressure value P of a pressure of the fresh concrete 10. In some embodiments, the pressure value P is measured by the rheological probe 18 in a manner that the computing device 32 receives the pressure value P from the rheological probe 18. In some embodiments, the viscosity value V is measured by a first rheological probe while the pressure value P is measured by a second rheological probe different from the first rheological probe.

At step 506, the computing device 32 accesses the calibration data sets $(Pr1, Wr1)_{Vr1}$ and $(Pr1, Wr2)_{Vr2}$. As mentioned above, the calibration data sets $(Pr1, Wr1)_{Vr1}$ and $(Pr1, Wr2)_{Vr2}$ include combinations of different reference pressure values Pr1 and Pr2 and associated reference workability values Wr1 and Wr2 for a corresponding one of the two reference viscosity values Vr1 and Vr2. As the calibration data sets $(Pr1, Wr1)_{Vr1}$ and $(Pr1, Wr2)_{Vr2}$ have been previously obtained through different calibration processes, these data can be stored on a memory accessible by the computing device 32. For instance, in this embodiment, the calibration data sets $(Pr1, Wr1)_{Vr1}$ and $(Pr1, Wr2)_{Vr2}$ are stored on a memory of the computing device 32 and the step 506 involves a processor of the computing device 32 accessing the calibration data sets $(Pr1, Wr1)_{Vr1}$ and $(Pr1, Wr2)_{Vr2}$ on the memory of the computing device 32.

It is noted that the memory of the computing device 32 can stored thereon more than just the two calibration data sets $(Pr1, Wr1)_{Vr1}$ and $(Pr1, Wr2)_{Vr2}$. Indeed, there can be a plurality of calibration data sets $(Prn, Wrn)_{Vrn}$, where n equals 1, 2, 3, 4, and so forth, to which the computing device 32 can have access to. In some embodiments, the computing device 32 selects the two calibration data sets $(Pr1, Wr1)_{Vr1}$ and $(Pr1, Wr2)_{Vr2}$ by comparing the measured viscosity value V to the reference viscosity values Vrn associated with each of the calibration data sets stored on the memory of the computing device 32. For instance, the computing device 32 selects the two calibration data sets $(Pr1, Wr1)_{Vr1}$ and $(Pr1, Wr2)_{Vr2}$ such that the measured viscosity value V is comprised between the reference viscosity value Vr1 and the reference viscosity value Vr2, i.e., Vr1<V<Vr2. When the measured viscosity value V cannot be comprised between the reference viscosity value Vr1 and the reference viscosity value Vr2, the two calibration data sets $(Pr1, Wr1)_{Vr1}$ and $(Pr1, Wr2)_{Vr2}$ are selected so as to be as close as possible to the measured viscosity value V. Indeed preferably, the two calibration data sets $(Pr1, Wr1)_{Vr1}$ and $(Pr1, Wr2)_{Vr2}$ are selected such that the reference viscosity values Vr1 and Vr2 minimize the differences |V−Vr1| and |Vr2−V|, wherein |( )| denotes the absolute value of 0, which can provide interpolation/extrapolation with a satisfactory accuracy. In some other embodiments, the computing device 32 selects the two calibration data sets $(Pr1, Wr1)_{Vr1}$ and $(Pr1, Wr2)_{Vr2}$ based on an input inputted into the user interface 34 as will be described below with reference to FIGS. 6 and 6A. For instance, the user input corresponds to a relative viscosity value of 3, so that the calibration data set $(Pr1, Wr1)_{Vr1}$ having a relative viscosity of 2 and the calibration data set $(Pr1, Wr2)_{Vr2}$ having a relative viscosity of 4 are chosen.

Referring back to FIG. 5, at step 508, the computing device 32 determines a viscosity difference value Rv by comparing the measured viscosity value V to the two reference viscosity values Vr1 and Vr2. For instance, in some embodiments, the viscosity difference value Rv is determined by comparing a difference between the measured viscosity value V and one of the at least two reference viscosity values Vr1 and Vr2 relatively to the two reference viscosity values Vr1 and Vr2. For instance, the viscosity difference value Rv can be given by a mathematical relation equivalent to the following mathematical relation Rv=(V−Vr1)/(Vr2−Vr1).

At step 510, the computing device 32 determines a workability value W of the workability of the fresh concrete based on the reference workability values Wr1 and Wr2 associated with reference pressure values Pr1 and Pr2 corresponding to the measured pressure value P in the calibration data sets $(Pr1, Wr1)_{Vr1}$ and $(Pr1, Wr2)_{Vr2}$.

Referring now to FIG. 5A, the computing device 32 includes one or more processors ("the processor 40") and one or more memories ("the memory 42") communicatively coupled to one another. More specifically, as shown, the processor 40 accesses the calibration data set $(Pr1, Wr1)_{Vr1}$, retrieves the reference pressure value Pr1 that corresponds to received pressure value P, and then outputs the reference workability value Wr1 which is associated with the retrieved reference pressure value Pr1. Similarly, the processor 40 accesses the calibration data set $(Pr2, Wr2)_{Vr2}$, retrieves the reference pressure value Pr2 that corresponds to received pressure value P, and then outputs the reference workability value Wr2 which is associated with the retrieved reference pressure value Pr2. Once the reference workability values Wr1 and Wr2 are retrieved, the computing device 32 determines the workability value W based on the retrieved workability values Wr1 and Wr2 and on the viscosity difference value Rv. For instance, in some embodiments, the workability value is given by a mathematical relation equivalent to the mathematical relation W=Wr1+Rv·(Wr2+Wr1).

An example of which is described with reference to the data of the first and second calibration tables 20 and 26 shown respectively in FIGS. 2 and 4, wherein the reference viscosity value Vr1 of the first calibration table 20 is 2 and the reference viscosity value Vr2 of the second calibration table 26 is 4, in arbitrary units. For instance, in this example, the viscosity value V is measured to be 3, and the pressure value P is measured to be 7 kPa. In this case, the computing device 32 determines that the viscosity difference value is given by Rv=(V−Vr1)/(Vr2−Vr1)=(3−2)/(4−2) which yields a viscosity difference value Rv of 0.50. The computing device 32 retrieves the workability value Wr1 of 18 cm based on the first calibration table 20 and on the pressure value P of 7 kPa and the workability value Wr2 of 15 cm based on the second calibration table 26 on the pressure value P. Accordingly, the computing device 32 can determine the workability value W to be given by Wr1+Rv·(Wr2−Wr1)=18+0.5 (15−18)=16.5 cm.

It will be understood that the steps 508 and 510 of the method 500 can be considered as a linear interpolation or a linear extrapolation based on the received pressure and viscosity values P and V and on the calibration data sets $(Pr1, Wr1)_{Vr1}$ and $(Pr1, Wr2)_{Vr2}$. Accordingly, in some embodiments, the workability value W is determined by interpolating between reference workability values associated with reference pressure values corresponding to the measured pressure value P and on the viscosity difference value Rv. Similarly, in embodiments where the measured pressure value P is outside the range comprising the reference pressure values, the workability value W is determined by extrapolating between the reference workability values associated with reference pressure values corresponding to the measured pressure value P and on the viscosity difference value Rv.

Referring back to FIG. 5, at step 512, the fresh concrete is handled based on the determined workability value W. For instance, other ingredients can be added to the fresh concrete or the fresh concrete can be further mixed or poured.

In some cases, the measured pressure value P may differ from any of the reference pressure values Pr1 and Pr2. Accordingly, an additional estimation step based on an interpolation and/or an extrapolation can be performed. More specifically, in some embodiments, the computing device determines a pressure difference value Rp by comparing the measured pressure value P to two of the reference pressure values Pr1 and Pr1' or Pr2 and Pr2'. More specifically, the pressure difference value Rp can be given by Rp=(P−Pr1)/(Pr2−Pr1). The computing device 32 then determines, using the first calibration data set $(Pr1,Wr1)_{Vr1}$, a first intermediate reference workability value Wr1$i$ based on reference workability values Wr1 and Wr1' associated with the two of the reference pressure values Pr1 and Pr1' and on the pressure difference value Rp. Similarly, the computing device 32 determines, using the second calibration data set $(Pr1,Wr2)_{Vr2}$, a second intermediate reference workability value Wr2$i$ based on reference workability values Wr2 and Wr2' associated with the two of the reference pressure values Pr2 and Pr2' and on the pressure difference value Rp. Then, the workability value W can be determined based on the first and second intermediate reference workability values Wr1$i$ and Wr2$i$ and on the viscosity difference value Vr.

An example of which is described with reference to the data of the first and second calibration tables 20 and 26 shown respectively in FIGS. 2 and 4, where the measured pressure value P differs from any of the reference pressure values Pr1 and Pr2. In this example, the reference viscosity value Vr1 of the first calibration table 20 is 2 (arbitrary units) and the reference viscosity value Vr2 of the second calibration table 26 is 4. For instance, in this example, the viscosity value V is measured to be 3 and the pressure value P is measured to be 13 kPa. In this case, the viscosity difference value is determined to be Rv=(V−Vr1)/(Vr2−Vr1)=(3−2)/(4−2)=0.50, the pressure difference value is given by Rp=(P−Pr1)/(Pr1'−Pr1)=(P−Pr2)/(Pr2'−Pr2)=(13−11)/(15−11)=0.50, the first intermediate workability value Wr1$i$ is determined to be Wr1$i$=Wr1+Rp (Wr1'−Wr1)=13+0.5(9−13)=11 cm based on the first calibration table 20, and the second intermediate workability value Wr2$i$ is given by Wr2$i$=Wr2+Rp (Wr2'−Wr2)=11+0.5(11−14)=9.5 cm based on the second calibration table 26. Accordingly, the workability value W can then be determined to be W=Wr1$i$+Rv (Wr2$i$−Wr1$i$)=11+0.5 (9.5−11)=10.25 cm.

FIG. 6 shows a flowchart of an example of a method 600 of handling fresh concrete. Description of the method 600 will be made with reference to the embodiment shown in FIG. 1. Accordingly, it is noted that the method 600 can be performed by the system 100 in order to determine a workability value W of the fresh concrete and to handle the fresh concrete based on the determined workability value W.

Similarly to step 504 of method 500, at step 602 of method 600, the computing device 32 receives a pressure value P of a pressure of the fresh concrete 10. In some embodiments, the pressure value P is measured by the rheological probe 18 in a manner that the computing device 32 receives the pressure value P from the rheological probe 18.

At step 604, the computing device 32 receives identification data ID indicating a viscosity of the fresh concrete. The identification data ID can be indicative of a specific mixture of fresh concrete, of a family of mixture of fresh concrete relative viscosity of the given fresh concrete, of a calibration data set or, equivalently, of a given relative viscosity. For instance, the identification data ID are indicative that the fresh concrete has a relative viscosity which is higher (e.g., relative viscosity value of 4) or lower (e.g., relative viscosity value of 1) than a standard viscosity value (e.g., relative viscosity value of 2). It is envisaged that, in some embodiments, the identification data ID are received at the user interface 34 in the form of a user input and that, in some other embodiments, the identification data ID are received from rheological probe 18 in the form of a measured viscosity value V.

At step 606, the computing device 32 accesses a plurality of calibration data sets $(Prn,Wrn)_{Vrn}$. The calibration data sets $(Prn,Wrn)_{Vrn}$ include combinations of different reference pressure values Prn and associated reference workability values Wrn for a corresponding one of a plurality of reference viscosity values Vrn.

At step 608, the computing device 32 selects one of the plurality of calibration data sets $(Prn,Wrn)_{Vrn}$ based on the identification data ID. For instance, the computing device 32 selects the calibration data set $(Pr1,Wr1)_{Vr1}$.

At step 610, the computing device 32 determines the workability value W indicative of a workability of the fresh concrete based on the received pressure value P and on the selected one of the calibration data sets $(Prn,Wrn)_{Vrn}$.

Referring now to FIG. 6A, the processor 40 of the computing device 32 selects the calibration data set $(Pr1,Wr1)_{Vr1}$ stored on the memory 42 based on the identification data ID. More specifically, in this example, the identification data ID indicate that the fresh concrete has a viscosity associated with the reference viscosity value Vr1 more than any of the reference viscosity value Vrn and accordingly the calibration data set $(Pr1,Wr1)_{Vr1}$ is selected by the processor 40. The identification data ID can be provided in the form of a relative viscosity received from a user interface, of a measured viscosity value or of a mixture of fresh concrete or family of mixtures of fresh concrete which is known to be associated with the reference viscosity value Vr1 or of a calibration data set. Once the right calibration data set $(Pr1,Wr1)_{Vr1}$ is selected, the processor 40 retrieves the reference pressure value Pr1 that corresponds to received pressure value P and then outputs the reference workability value Wr1 which is associated with the retrieved reference pressure value Pr1. The computing device then determines the workability value W by setting the retrieved workability value Wr1 as the workability value W.

Referring back to FIG. 6, at step 612, the fresh concrete is handled based on the determined workability value W. For instance, other ingredients can be added to the fresh concrete or the fresh concrete can be further mixed or poured.

FIG. 7 shows a schematic representation of an example implementation of the methods 500, 600 and/or 900 (see FIG. 9) as a combination of software and hardware components. The computing device 32 is illustrated with the processor 40 and a memory 42 having stored thereon program instructions 50 configured to cause the processor 40 to generate one or more outputs based on one or more inputs. The inputs can comprise one or more signals representative of the pressure value P, the viscosity value V and/or the identification data ID. The outputs can comprise one or more signals representative of the workability value W.

The processor 40 can comprise any suitable devices configured to cause a series of steps to be performed so as to implement the methods 500, 600 and/or 900 such that instructions 50, when executed by the computing device 32 or other programmable apparatus, can cause functions/acts/steps specified in the methods described herein to be executed. The processor 40 can comprise, for example, any type of general-purpose microprocessor or microcontroller, a digital signal processing (DSP) processor, a central processing unit (CPU), an integrated circuit, a field programmable data array (FPGA), a reconfigurable processor, other suitably programmed or programmable logic circuits, or any combination thereof.

The memory 42 can comprise any suitable known or other machine-readable storage medium. The memory 42 can comprise non-transitory computer readable storage medium such as, for example, but not limited to, an electronic, magnetic, optical, electromagnetic, infrared, or semiconductor system, apparatus, or device, or any suitable combination of the foregoing. The memory 42 can include a suitable combination of any type of computer memory that is located either internally or externally to devices such as, for example, random-access memory (RAM) read-only memory (ROM), compact disc read-only memory (CDROM), electro-optical memory, magneto-optical memory, erasable programmable read-only memory (EPROM), and electrically-erasable programmable read-only memory (EEPROM), ferroelectric RAM (FRAM) or the like. Memory 42 can comprise any storage means (e.g., devices) suitable for retrievably storing machine-readable instructions executable by the processor 42.

Referring now to FIG. 8, in some embodiments, the computing device 32 can be accessible remotely from any one of a plurality of external devices 52 over connections 54. External devices 52 can have an application, or a combination thereof, for accessing the computing device 32. Alternatively, the external devices 52 can access the computing device 32 via a web application, e.g., accessible through any type of web browser.

The connections 54 can comprise wire-based technology, such as electrical wires or cables, and/or optical fibers. The connections 54 can also be wireless, such as RF, infrared, Wi-Fi, Bluetooth, and others. The connections 54 can therefore comprise a network, or others known to those skilled in the art. Communication over the network can occur using any known protocols that enable external devices 52 within a computer network to exchange information. The examples of protocols are as follows: IP (Internet Protocol), UDP (User Datagram Protocol), TCP (Transmission Control Protocol), DHCP (Dynamic Host Configuration Protocol), HTTP (Hypertext Transfer Protocol), FTP (File Transfer Protocol), Telnet (Telnet Remote Protocol), or SSH (Secure Shell Remote Protocol).

In some embodiments, the computing device 32 is provided at least in part on any one of external devices 52. For example, the computing device 32 can be configured as a first portion provided in the system 100 to obtain and transmit the pressure value P and/or the viscosity value V to a second portion, provided on one of the external devices 52. The second portion can be configured to receive the pressure value P and/or the viscosity value V and perform any one of steps 506-510 of method 500 and/or steps 606-610 of method 600 on one of the external devices 52. Alternatively, the computing device 32 is provided entirely on any one of the external devices 52 and is configured to receive from the pressure value P and/or the viscosity value V.

One or more databases 56, such as memory 42 can be provided locally on any one of the computing device 32 and the external devices 52, or can be provided separately therefrom (as illustrated). In the case of a remote access to the databases 56, access can occur via the connections 54 taking the form of any type of network, as indicated above. The various databases 56 described herein can be provided as collections of calibration data sets or information organized for rapid search and retrieval by a computer. The databases 56 can be structured to facilitate storage, retrieval, modification, and deletion of data on a data storage medium, such as one or more servers. The databases 56 illustratively have stored therein raw data representing a plurality of features of the system 100, the features being, for example, the calibration data sets $(Prn, Wrn)_{Vrn}$ or the relationship between specific mixtures of fresh concrete (or families thereof) and their respective reference viscosity Vr.

Each computer program described herein can be implemented in a high level procedural or object oriented programming or scripting language, or a combination thereof, to communicate with a computer system. Alternatively, the programs can be implemented in assembly or machine language. The language can be a compiled or interpreted language. Computer-executable instructions can be in many forms, including program modules, executed by one or more computers or other devices. Generally, program modules include routines, programs, objects, components, data structures, etc., that perform particular tasks or implement particular abstract data types. Typically the functionality of the program modules can be combined or distributed as desired in various embodiments.

FIG. 9 shows an example of a flowchart 900 for determining one or more workability values W of a workability of fresh concrete, in accordance with an embodiment. FIG. 9 will be described with reference to the embodiment shown in FIG. 1.

As depicted, at step 902, the computing device 32 determines whether some conditions are met to measure workability. Examples of such conditions can include whether or not the rotation speed of the drum 12 or a tangential speed of the probe exceeds a corresponding threshold (e.g., 0.75 m/s) and whether or not the level of fresh concrete inside the drum 12 exceeds a threshold. Some other conditions can also be used.

At step 904, the computing device 32 determines whether identification data ID concerning the fresh concrete are available. If no identification data ID are available, the computing device 32 goes at step 906. If identification data ID are available, the computing device 32 goes at step 908.

At step 906, the computing device 32 verifies whether a viscosity value V is received (e.g., measured). If a viscosity value V is received at the computing device 32, at step 910, the computing device 32 selects one of a plurality of calibration data sets having different reference viscosity values stored on a memory based on the received viscosity value V. At step 910, if the selected calibration data set is expressed in terms of slump, spread and/or slump flow, the workability value W is determined accordingly in terms of slump, spread and/or slump flow. For instance, the reference workability values Wr1 and Wr2 are expressed in terms of slump in FIGS. 2 and 4. However, it is envisaged that these reference workability values Wr1 and Wr2 can, additionally or alternatively, be expressed in terms of either spread or slump flow.

If a viscosity value V is not received at the computing device 32, at step 912, the computing device 32 determines the workability value W based on the standard calibration data set, e.g., the first calibration table 20 shown in FIG. 2. At step 912, since the standard calibration data set is generally expressed in terms of slump, spread and/or slump flow, the workability value W is determined accordingly in terms of slump, spread and/or slump flow.

At step 908, the computing device 32 determines whether a specific calibration data set is provided, e.g., inputted at the user interface 34. If a specific calibration data set is provided, at step 914, the computing device 32 determines the workability value W based on the provided calibration data set. If no specific calibration data set is provided, at step 916, the computing device 32 determines whether the workability value is expected to be expressed in terms of slump, spread and/or slump flow.

If there is no indication on which of the workability tests is preferred, the computing device 32 goes at step 912 and determines the workability value W in terms of slump, spread and/or slump flow based on the standard calibration data set.

If there is an indication on which of the workability tests is preferred, the computing device goes at step 918. At step 918, the computing device 32 determines if a viscosity value V has been received. If a viscosity value V has not been received, the computing device 32 goes at step 920 and if a viscosity value V has in fact been received, the computing device 32 goes at step 922.

At step 920, the computing device 32 determines the workability value W based on the standard calibration data set and outputs it in the form of the preferred workability test (e.g., slump, spread or slump flow).

At step 922, the computing device 32 selects one of a plurality of calibration data sets having different reference viscosity values stored on a memory based on the received viscosity value V, determines the workability value based on the selected calibration data set and outputs it in the form of the preferred workability test (e.g., slump, spread or slump flow).

As can be understood, the examples described above and illustrated are intended to be exemplary only. As shown in the figures, the concrete mixer receiving the system can be in the form of the mixer truck. In another embodiment, the system can be mounted to another form of concrete mixer, such as a stationary mixer of a concrete production plant. In some embodiments, the computing device is enclosed inside a housing of the rheological probe 18 and the determined workability value is transmitted to the user interface via a wired or wireless connection. The expression "calibration data sets" is meant to be construed broadly so as to encompass data stored in the form of table, array, or even in the form of mathematical relations. The two or more calibration data sets can also be provided in the form of a single calibration set wherein combinations for a corresponding one of the at least two viscosity reference values can be retrieved by the processor (e.g., one matrix having three columns for a respective one of reference viscosity values Vr, reference pressure values Pr and workability values Wr). The scope is indicated by the appended claims.

What is claimed is:

1. A method of handling fresh concrete comprising:
receiving a viscosity value (V) of the fresh concrete (10) and a pressure value (P) of a pressure exerted on a rheological probe (18) moving in the fresh concrete (10);
using a processor (40),
accessing at least two calibration data sets, the at least two calibration data sets Including combinations of different reference pressure values (Pr1, Pr2) and associated reference workability values (Wr1, Wr2) for a corresponding one of at least two reference viscosity values (Vr1, Vr2) different from said received viscosity value (V);
determining a viscosity difference value (Rv) by comparing the received viscosity value (V) to the at least two reference viscosity values (Vr1, Vr2); and
determining a workability value (W) of the workability of the fresh concrete (10) based on the reference workability values (Wr1, Wr2) associated with reference pressure values (Pr1, Pr2) corresponding to the received pressure value (P) in the at least two calibration data sets and on the viscosity difference value (Rv); and
handling the fresh concrete (10) based on the determined workability value (W).

2. The method of claim 1 wherein said comparing includes comparing a difference between the received viscosity value (V) and one of the at least two reference viscosity values (Vr1, Vr2) relatively to the at least two reference viscosity values (Vr1, Vr2).

3. The method of claim 1 wherein said determining the workability value (W) includes interpolating between the reference workability values (Wr1, Wr2) associated with reference pressure values (Pr1, Pr2) corresponding to the received pressure value (P) and on the viscosity difference value (Rv).

4. The method of claim 1 wherein said receiving the viscosity value (V) includes measuring, using the rheological probe (18), the viscosity value of the fresh concrete (10).

5. The method of claim 1 wherein said receiving the pressure value (P) includes measuring, using the rheological probe (18), the pressure value of a pressure exerted on the rheological probe (18) by the fresh concrete (10) when the rheological probe (18) is moved at a tangential speed comprised in a low speed range.

6. The method of claim 1 wherein the reference workability value (Wr1, Wr2) and the determined workability value (W) are provided In the form of slump values.

7. The method of claim 1 wherein the received pressure value (P) differs from any one of the reference pressure values (Pr1, Pr2), the method further comprising:
determining a pressure difference value (Rp) by comparing the received pressure value (P) to at least two of the reference pressure values (Pr1, Pr2);
determining, using one of the at least two calibration data sets, a first intermediate reference workability value (Wr1i) based on reference workability values (Wr1, Wr2) associated with the at least two of the reference pressure values (Pr1, Pr2) and on the pressure difference value (Rp); and
determining, using another one of the at least two calibration data sets, a second intermediate reference workability value (Wr2i) based on reference workability values (Wr1, Wr2) associated with the at least two of the reference pressure values (Pr1, Pr2) and on the pressure difference value (Rp);

wherein said determining the workability value (W) including determining the workability value of the fresh concrete (10) based on the first and second intermediate reference workability values (Wr1i, Wr2i) and on the viscosity difference value (Rv).

8. The method of claim 1 wherein said handling the fresh concrete (10) includes adding ingredients to the fresh concrete (10).

9. The method of claim 1 wherein said handling the fresh concrete (10) includes pouring the fresh concrete (10).

10. A system comprising:
   at least one rheological probe (18) mounted to a concrete mixer, the rheological probe (18) being configured to measure a pressure value (P) of a pressure exerted on the at least one rheological probe (18) moving in fresh concrete (10) inside the concrete mixer;
   a computing device (32) communicatively coupled with the theological probe (18), the computing device (32) being configured for performing the steps of receiving a viscosity value (V) of the fresh concrete (10);
   accessing at least two calibration data sets stored on a memory accessible by the computing device (32), the at least two calibration data sets including combinations of different reference pressure values (Pr1, Pr2) and associated reference workability values (Wr1, Wr2) for a corresponding one of at least two reference viscosity values (Vr1, Vr2) different from said received viscosity value (V);
   determining a viscosity difference value (Rv) by comparing the received viscosity value (V) to the at least two reference viscosity values (Vr1, Vr2); and
   determining a workability value (W) of the workability of the fresh concrete (10) based on the reference workability values (Wr1, Wr2) associated with reference pressure values (Pr1, Pr2) corresponding to the measured pressure value (P) In the at least two calibration data sets and on the viscosity difference value (Rv); and
   a user interface (34) communicatively coupled with the computing device (32), the user interface (34) being configured to output a signal indicative of the workability value (W) of the fresh concrete (10).

11. The system of claim 10 wherein the computing device (32) is enclosed in the theological probe (18).

12. The system of claim 10 wherein the theological probe (18) includes a transmitter for transmitting the measured pressure value (P) to the computing device (32).

13. The system of claim 10 wherein the rheological probe (18) is configured to measure the viscosity value (V), the viscosity value (V) being received by the computing device (32) from the rheological probe (18).

14. The system of claim 10 wherein the viscosity value (V) is received from the user interface (34).

* * * * *

UNITED STATES PATENT AND TRADEMARK OFFICE
CERTIFICATE OF CORRECTION

PATENT NO. : 11,420,358 B2
APPLICATION NO. : 16/468473
DATED : August 23, 2022
INVENTOR(S) : Denis Beaupre It is certified that error appears in the above-identified patent and that said Letters Patent is hereby corrected as shown below:

On the Title Page

Item (57) Abstract, Line 3, delete "Theological" and replace with --rheological--.

In the Claims

At Column 14, Claim number 1, Line number 9, delete "Including" and replace with --including--.
At Column 14, Claim number 6, Line number 49, delete "In" and replace with --in--.
At Column 15, Claim number 10, Line number 18, delete "theological" and replace with --rheological--.
At Column 16, Claim number 10, Line number 8, delete "In" and replace with --in--.
At Column 16, Claim number 11, Line number 16, delete "theological" and replace with --rheological--.
At Column 16, Claim number 12, Line number 17, delete "theological" and replace with --rheological--.

Signed and Sealed this
First Day of November, 2022

Katherine Kelly Vidal
*Director of the United States Patent and Trademark Office*